US011854428B2

(12) United States Patent
Song et al.

(10) Patent No.: US 11,854,428 B2
(45) Date of Patent: Dec. 26, 2023

(54) TACTILE DISPLAY APPARATUS FOR PALPATION SIMULATION AND TELEMEDICINE AND METHODS OF USE

(71) Applicant: University of Central Florida Research Foundation, Inc., Orlando, FL (US)

(72) Inventors: Sang-Eun Song, Orlando, FL (US); Sakura Sikander, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 18/076,603

(22) Filed: Dec. 7, 2022

(65) Prior Publication Data

US 2023/0098091 A1    Mar. 30, 2023

Related U.S. Application Data

(63) Continuation of application No. 16/818,672, filed on Mar. 13, 2020, now Pat. No. 11,538,362.

(Continued)

(51) Int. Cl.
*G09B 23/28* (2006.01)
*G09B 23/32* (2006.01)

(Continued)

(52) U.S. Cl.
CPC ............. *G09B 23/32* (2013.01); *G06F 3/016* (2013.01); *G08C 17/02* (2013.01); *G16H 40/67* (2018.01);

(Continued)

(58) Field of Classification Search
CPC ........ G09B 23/32; G16H 40/67; G16H 50/50; G16H 50/20; G06F 3/016; G08C 17/02; G08C 2201/93

(Continued)

(56) References Cited

U.S. PATENT DOCUMENTS

| | | | |
|---|---|---|---|
| 2012/0235935 A1* | 9/2012 | Ciesla | G06F 3/047 345/173 |
| 2018/0157317 A1* | 6/2018 | Richter | G06T 19/006 |
| 2020/0184791 A1* | 6/2020 | Hall, Jr. | G08B 21/02 |

OTHER PUBLICATIONS

Williams II, et al. The Virtual Haptic Back for Palpatory Training. 2004. ICMI' 04: 191-197.

(Continued)

*Primary Examiner* — Naomi J Small
(74) *Attorney, Agent, or Firm* — Owen G. Behrens; Smith & Hopen, P.A.

(57) ABSTRACT

A tactile display device including a nodule having variable stiffness under a surface to provide a near-real feeling of palpation for a physician. The device utilizes granular jamming technology using pneumatic actuation to control a nodule that maintains its shape while allowing the modulation in stiffness. The nodule includes two hemispheres, a contact portion and an actuation portion, forming a sphere. The contact portion and the actuation portion include different thicknesses and/or materials, while the dimensions of the dimensions of the nodule are maintained. As such, a physician can utilize the device to identify the difference between a normal lump and an affected lump even if the shape of each lump appears to be the same. With the tactile display device, due to the different levels of stiffness, a physician can detect the severity of the lump.

20 Claims, 10 Drawing Sheets

Related U.S. Application Data

(60) Provisional application No. 62/817,853, filed on Mar. 13, 2019.

(51) Int. Cl.
    *G06F 3/01*         (2006.01)
    *G16H 40/67*      (2018.01)
    *G16H 50/50*      (2018.01)
    *G08C 17/02*      (2006.01)
    *G16H 50/20*      (2018.01)

(52) U.S. Cl.
    CPC .......... *G16H 50/50* (2018.01); *G08C 2201/93* (2013.01); *G16H 50/20* (2018.01)

(58) Field of Classification Search
    USPC ........................................................ 434/267
    See application file for complete search history.

(56) References Cited

OTHER PUBLICATIONS

Jeon et al., Haptic simulation of breast cancer palpation: A case study of haptic augmented reality. IEEE International Symposium on Mixed and Augmented Reality. 2010. 237-38.

Baillie et al., Validation of a bovine rectal palpation simulator for training veterinary students. Stud. Health Technol. Inform. 2005. vol. 111. 33-36.

Takaiwa and Noritsugu. Development of breast cancer palpation simulator using pneumatic parallel manipulator. SICE Annual Conference. 2007: 823-827.

Gwilliam et al., Design and control of an air-jet lump display. 2012 IEEE Haptics Symposium (HAPTICS). 2012: 45-49.

Li et al., A tactile sensing and feedback system for tumor localization. 2016 13th International Conference on Ubiquitous Robots and Ambient Intelligence (URAI). 2016: 259-262.

Li et al., Multi-fingered haptic palpation utilizing granular jamming stiffness feedback actuators. Smart Mater. Struct. 2014. vol. 23: 095007.

Stanley et al., Closed-loop shape control of a haptic jamming deformable surface. 2016 IEEE International Conference on Robotics and Automation (ICRA). 2016: 2718-2724.

Liu et al., Jamming is not just cool any more. Nature. 1998. vol. 396: 21-22.

Jiang et al., Robotic granular jamming: Does the membrane matter? Soft. Robot. 2014. vol. 1 (No. 3): 192-201.

Cheng et al., Design an analysis of a robust, low-cost, highly articulated manipulator enabled by jamming of granular media. 2012 IEEE International Conference on Robotics and Automation. 2012: 4328-33.

Cox and Erler. Remodeling and homeostasis of the extracellular matrix: implications for fibrotic diseases and cancer. Dis. Model. Mech. 2011. vol. 4: 165-178.

\* cited by examiner

TACTILE DISPLAY APPARATUS FOR PALPATION SIMULATION AND TELEMEDICINE AND METHODS OF USE

CROSS-REFERENCE TO RELATED APPLICATIONS

This nonprovisional patent application is a continuation of and claims the benefit of U.S. patent application Ser. No. 16/818,672, entitled "TACTILE DISPLAY APPARATUS FOR PALPATION SIMULATION AND TELEMEDICINE AND METHODS OF USE" filed Mar. 13, 2020, by the same inventors, which claims priority to U.S. Provisional Patent Application No. 62/817,853 entitled "TACTILE DISPLAY APPARATUS FOR PALPATION SIMULATION AND TELEMEDICINE AND METHODS OF USE" filed Mar. 13, 2019 by the same inventors, all of which are incorporated herein by reference, in their entireties, for all purposes.

BACKGROUND OF THE INVENTION

1. Field of the Invention

This invention relates, generally, to display apparatuses used in combination with simulations and remote applications. More specifically, it relates to a tactile display apparatus and associated methods of use for palpation simulation and palpation telemedicine, thereby enabling users to receive sensations from remote sources similar to those typically received from live, point-of-care patients.

2. Brief Description of the Prior Art

Tissue palpation is one of the fundamental steps used by physicians for routine examinations or early diagnosis of diseases (for example, physical inspection of thyroid nodules or cancerous tumors). These nodules or tumors are stiffer than normal tissues, and such a nodule or tumor presents as a rigid mass inside of a compliant tissue. Manual palpation enables a physician or care provider to perceive the variation in stiffness typically associated with nodules or tumors within normal tissues. In general, by performing palpation, a physician receives feedback regarding the texture, size, and stiffness of the tissue—these elements are key in the primary diagnostic procedure. For example, differences in the size and stiffness of a lesion can provide information about the initiation of a disease or its severity by helping to differentiate a benign tumor from a malignant tumor [1-2].

As soon as a physician or other care provider begins his or her medical practice, it is essential that the physician has enough experience using palpation as a tool for preliminary diagnosis. However, in reality, obtaining such experience may not always be possible due to limited training time and methods. The gap between the skillsets of physicians and the ideal skill levels can be bridged by providing a training device that can provide the sensation of touch along with variation in size and stiffness of the tumors or tissues, similar to those found in real patients. A tactile display unit can also be integrated with a telemedicine system enabling physicians to receive a sensation similar to palpation from remotely located patients.

A number of tactile display simulators for medical palpation have been developed, including systems with conventional haptic devices [3-5], as well as pneumatic simulators that use controllable air pressure for simulating soft tissue stiffness [6-8]. For example, a combination of granular jamming and pneumatics has been utilized in a multi-finger haptic palpation device to show its superiority over a single point feedback [9]. In the study, ground coffee was used inside the granular jamming chamber to create the shape of an indenter (i.e., the fingertip) for varying stiffness feedback. Another approach using pneumatics and granular jamming demonstrated deformable geometry and variable stiffness using an array of cells with a distinct sequence of air pressure and vacuum levels [10]. The approach allows regions of the surface to display a different combination of lump sizes and stiffness.

However, in the approach of [10] and the relevant prior art, no attempt has been made to maintain the shape of a studied mass while stiffness of the mass varied. Such a phenomenon is important for palpation since a nodule with a particular shape can be malignant or benign depending on its stiffness property. Accordingly, what is needed is a device that can enable the identification of the differences between a normal lump and an affected lump, even if the dimensions of both lumps are the same, thereby forming a part of a palpation training device. Also, what is needed is a realistic tactile display in communication with a device capable of providing a near-real sensation of touch similar to a human palpation. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Tissue palpation is one of the fundamental steps used by physicians for routine examinations or early diagnosis of diseases (for example, physical inspection of thyroid nodules or cancerous tumors). These nodules or tumors are stiffer than normal tissues, and such a nodule or tumor presents as a rigid mass inside of a compliant tissue. Manual palpation enables a physician or care provider to perceive the variation in stiffness typically associated with nodules or tumors within normal tissues. In general, by performing palpation, a physician receives feedback regarding the texture, size, and stiffness of the tissue—these elements are key in the primary diagnostic procedure. For example, differences in the size and stiffness of a lesion can provide information about the initiation of a disease or its severity by helping to differentiate a benign tumor from a malignant tumor [1-2].

As soon as a physician or other care provider begins his or her medical practice, it is essential that the physician has enough experience using palpation as a tool for preliminary diagnosis. However, in reality, obtaining such experience may not always be possible due to limited training time and methods. The gap between the skillsets of physicians and the ideal skill levels can be bridged by providing a training device that can provide the sensation of touch along with variation in size and stiffness of the tumors or tissues, similar to those found in real patients. A tactile display unit can also be integrated with a telemedicine system enabling physicians to receive a sensation similar to palpation from remotely located patients.

A number of tactile display simulators for medical palpation have been developed, including systems with conventional haptic devices [3-5], as well as pneumatic simulators that use controllable air pressure for simulating soft tissue stiffness [6-8]. For example, a combination of granular jamming and pneumatics has been utilized in a multi-finger haptic palpation device to show its superiority over a single point feedback [9]. In the study, ground coffee was used inside the granular jamming chamber to create the shape of an indenter (i.e., the fingertip) for varying stiffness feedback. Another approach using pneumatics and granular jamming demonstrated deformable geometry and variable stiffness using an array of cells with a distinct sequence of air pressure and vacuum levels [10]. The approach allows regions of the surface to display a different combination of lump sizes and stiffness.

However, in the approach of [10] and the relevant prior art, no attempt has been made to maintain the shape of a studied mass while stiffness of the mass varied. Such a phenomenon is important for palpation since a nodule with a particular shape can be malignant or benign depending on its stiffness property. Accordingly, what is needed is a device that can enable the identification of the differences between a normal lump and an affected lump, even if the dimensions of both lumps are the same, thereby forming a part of a palpation training device. Also, what is needed is a realistic tactile display in communication with a device capable of providing a near-real sensation of touch similar to a human palpation. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1A:
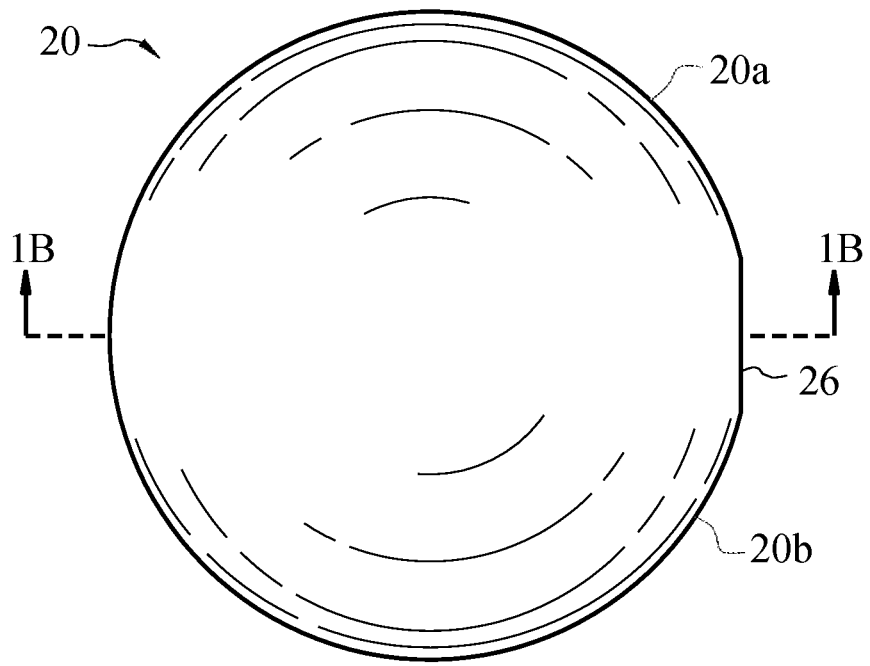
FIG. 1A is a close-up orthogonal view of a nodule in accordance with an embodiment of the present invention, including section line A-A.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes a tactile display device including a nodule of a given size with variable stiffness under a surface to provide a near-real feeling of palpation for a physician. The device utilizes granular jamming technology using pneumatic actuation to control a display nodule that maintains its shape while allowing the modulation in stiffness. Accordingly, the present invention includes a hemispherically-combined display nodule including a contact portion and an actuation portion, forming a sphere. The display nodule includes a different thickness and material for the contact portion and for the actuation portion. The device provides a controllable tactile display while maintaining the dimensions of the nodule. As such, a physician can utilize the device to identify the difference between a normal lump and an affected lump even if the shape of each lump appears to be the same. With the tactile display device, due to the different levels of stiffness, a physician can detect the severity of the lump. The tactile display can be refined and improved by collecting design and feasibility feedback from users, including medical experts/physicians.

As discussed in the background section above, attempts have been made to utilize granular jamming to produce devices capable of be used to diagnose varying thicknesses on a target area. The field of granular jamming has been significantly growing in robotics, providing a structural stiffening method useful in stiffness modulation [9]. The mechanism of jamming enables phase transition of a grained substance in response to an external stress [11-12]. In general, a granular jamming apparatus includes granules, a flexible membrane for enclosing the granules, and a pneumatic pump for providing vacuum pressure [12]. Different kinds of granules can be used for jamming depending on the purpose of the device, including couscous, rice, coffee, sand, glass beads, and other small and relatively course substances. For example, coffee grounds are ideal materials for use in combination with granular jamming due to the irregularity in shape of the individual coffee grounds. As such, the coffee grounds can jam together under the application of vacuum pressure [9], [13]. Under normal conditions, the granules can move freely within the membrane providing the sensation of a soft and flexible object. When vacuum pressure is applied within the membrane, the membrane jams granules together and provides the sensation of a stiffer object. Since vacuum pressure can be regulated to control the amount or level of granular jamming, the device can provide the sensation of varying levels of stiffness depending on the level of vacuum pressure applied.

Figure 1B:
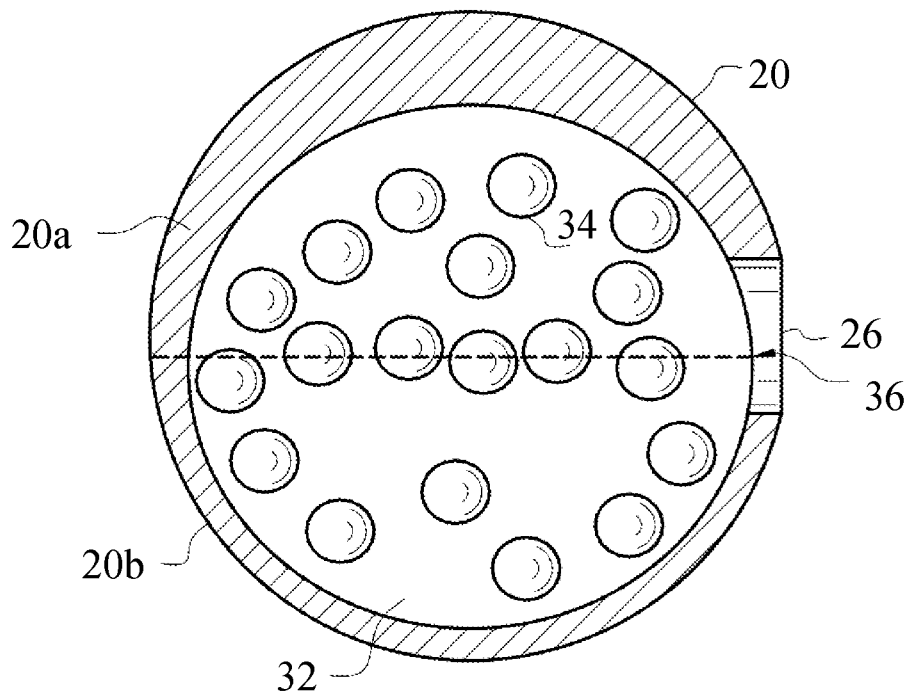
FIG. 1B is a cross-sectional view of the nodule of FIG. 1A along section line A-A.

Accordingly, as shown in FIGS. 1A-1B, an embodiment of tactile nodule 20 includes a first portion 20a and a second portion 20b. To sufficiently mimic the shape of a real-life nodule on a patient, in an embodiment tactile nodule 20 is substantially spherical, including a top hemisphere (first portion 20a) and a bottom hemisphere (second portion 20b). Accordingly, first portion 20a may be referred to as top hemisphere 20a, and second portion 20b may be referred to as bottom hemisphere 20b. However, it should be appreciated that nodules of various geometries can be replicated in tactile nodule 20.

Tactile nodule 20 includes a separation between top hemisphere 20a and bottom hemisphere 20b that is denoted by reference numeral 36 in FIG. 1B. To separate top hemisphere 20a from bottom hemisphere 20b, nodule 20 can be formed by two separate hemispherical components. Alternatively, nodule 20 can consist of a singular piece of material, with the separation 36 of top hemisphere 20a from bottom hemisphere 20b being accomplished via a wall or membrane disposed within nodule 20. By separating nodule 20 into different hemispheres, varying stiffnesses, thicknesses, and materials can be associated with the different hemispheres, allowing for more particular diagnostics.

For example, in an embodiment, bottom hemisphere 20b is made from the same material as top hemisphere 20a (i.e., Material_A); however, bottom hemisphere 20b is made of a thinner layer of the material than top hemisphere 20a (i.e., $t\_A > t\_B$). In such an embodiment, greater deformation of bottom hemisphere 20b can be accomplished as compared with top hemisphere 20a. In another embodiment, top hemisphere 20a is made of Material_A and bottom hemisphere 20b is made of Material_B, with equal thicknesses. In such an embodiment, Material_A may be stiffer than Material_B; as such, there is greater deformation of bottom hemisphere 20b as compared with top hemisphere 20a. In yet another embodiment, top hemisphere 20a includes Material_A and thickness $t\_A$, and bottom hemisphere 20b includes Material_B and thickness $t\_B$, with $t\_A > t\_B$. In such an embodiment, a very high degree of deformation of bottom hemisphere 20b may be accomplished.

Also as shown in FIGS. 1A-1B, inlet 26 provides a port or channel through which the airflow and pressure within nodule 20 can be varied and modified. As shown in particular in FIG. 1B, nodule 20 defines cavity 32 defined by the interior surfaces of each of top hemisphere 20a and bottom hemisphere 20b. Accordingly, the pressure within cavity 32 can be controlled by a pneumatic control unit via inlet 26; for example, if a pneumatic control unit removes a portion of the air within cavity 32, nodule 20 will deform. As used herein, "deform" means capable of changing shape in response to a stress or force while also being capable of regaining an original shape in the absence of the stress of force. If the material properties of top hemisphere 20a and bottom hemisphere 20b are equal, the deformation is uniform throughout cavity 32 and nodule 20. However, if the material properties differ between the hemispheres, deformation is nonuniform. Specifically, if top hemisphere 20a has a thickness greater than that of bottom hemisphere 20b, a greater degree of deformation is experienced by bottom hemisphere 20b than by top hemisphere 20a. The relationship between the hemispheres and their materials and physical properties will be discussed in greater detail below.

Moreover, a plurality of granules 34 are disposed within cavity 32, with the plurality of granules 34 being used in the diagnostic testing provided by utilizing nodule 20. As discussed above, the plurality of granules 34 are used in a granular jamming implementation within nodule 20, in which the displacement of the plurality of granules 34 differs depending on the pressure value within nodule 20, as well as the materials and physical properties of top hemisphere 20a and bottom hemisphere 20b. Accordingly, in the example discussed above (in which top hemisphere 20a and bottom hemisphere 20b have equivalent material properties), the plurality of granules 34 will be squeezed uniformly from the interior surfaces of nodule 20, and will change the stiffness and shape of nodule 20 in a relatively uniform manner. In the alternative example discussed above (in which top hemisphere 20a has a thickness greater than that of bottom hemisphere 20b), the plurality of granules 34 are condensed toward a central portion of cavity 32 and toward the inner surfaces of top hemisphere 20a due to the greater degree of deformation experienced by bottom hemisphere 20b. As such, regardless of the materials and thicknesses used on nodule, under the same vacuum pressure within cavity 32 of nodule 20, bottom hemisphere 20b deflates inward toward top hemisphere 20a to compensate for the change in pressure air is removed from cavity 32, such as by a pneumatic control unit. Top hemisphere experiences minimal effects resulting from the vacuum pressure, and the plurality of granules 34 experience forces that squeeze granules 34 toward top hemisphere 20a due to the deflection of bottom hemisphere 20b.

Figure 1C:
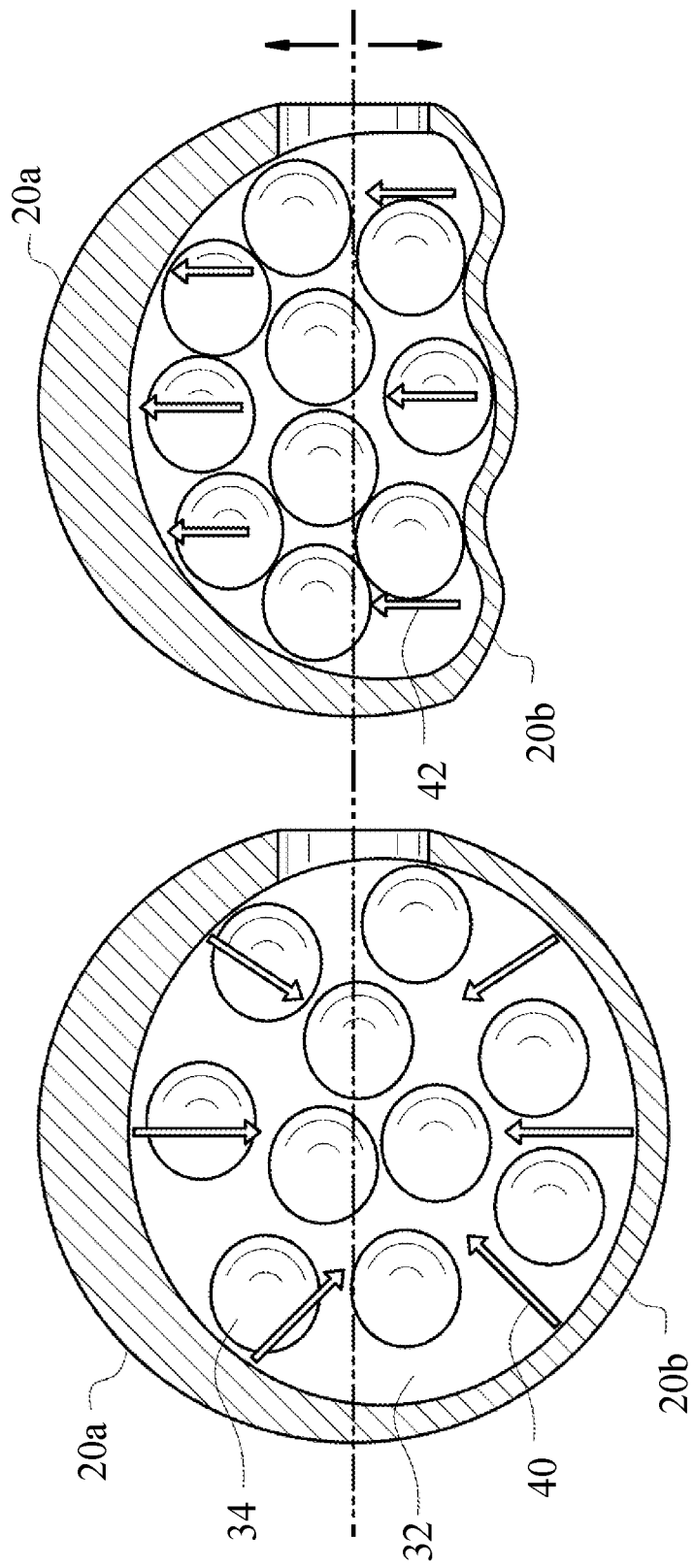
FIG. 1C is an internal orthogonal view of the nodule of FIG. 1A along section line A-A in both an inflated state and in a deflated state.

FIG. 1C depicts an embodiment of nodule 20 that is an ideal tactile nodule for diagnostic testing via a tactile display device. During diagnostic palpation of nodule 20, it is desired that top hemisphere 20a of nodule 20 maintain an original shape without deforming, since top hemisphere 20a is designed to mimic a skin side of a mass within a patient, and since palpation is performed on the skin side of a mass. Accordingly, in the example shown in FIG. 1C, bottom hemisphere 20b is made of a material that is more deformable than a material of which top hemisphere 20a is made, making top hemisphere 20a minimally deformable during palpation. Accordingly, when a pneumatic control unit removes a portion of the air within cavity 32 of nodule 20, bottom hemisphere 20b deflates, and the plurality of granules 34 translate toward the inner surfaces of top hemisphere 20a, as discussed above. As such, when positive air pressure fills cavity 32, such as the example shown on the left side of FIG. 1C, relatively equal inward normal forces (denoted by reference numeral 40) act on cavity 32 and the plurality of granules 34 disposed within cavity 32. However, when a pneumatic control unit removes air from cavity, the vacuum pressure resulting from the removal of air transforms the inward normal forces to outward normal reaction forces (denoted by reference numeral 42) on top hemisphere 20a. The change in direction of force and the effects of the force on the plurality of granules 34 are keys factors in changing the stiffness of top hemisphere 20a, and of nodule 20 in general. As such, the combination of granular jamming together with different properties for top hemisphere 20a and bottom hemisphere 20b enables a change in stiffness of top hemisphere 20a without a change in shape of top hemisphere 20a, allowing top hemisphere 20a to mimic a mass within a patient.

Figure 2A:
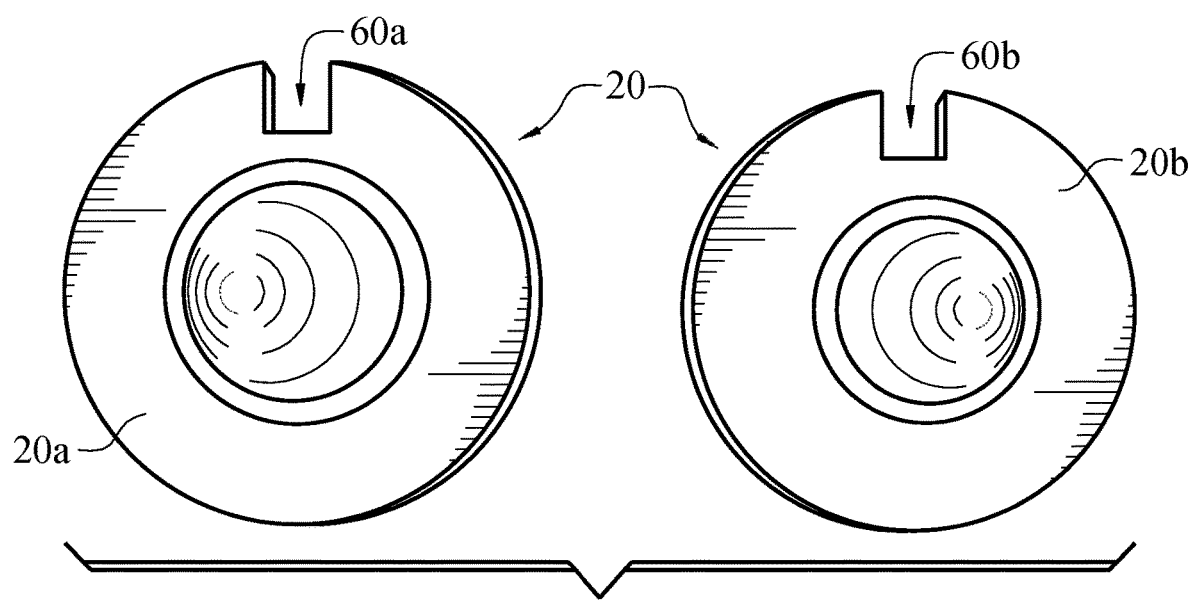
FIG. 2A is an orthogonal view of a disassembled nodule in accordance with an embodiment of the present invention.
Figure 2B:
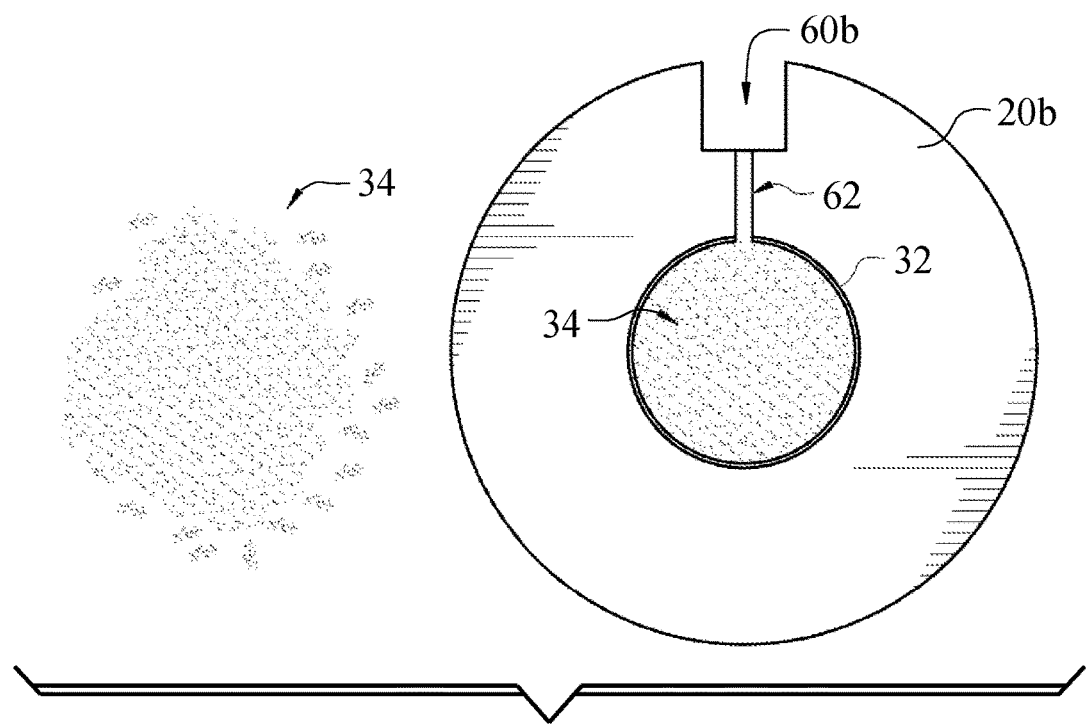
FIG. 2B is a top plan view of a bottom hemisphere of the nodule FIG. 2A include a plurality of granules within a cavity of the nodule.
Figure 2C:
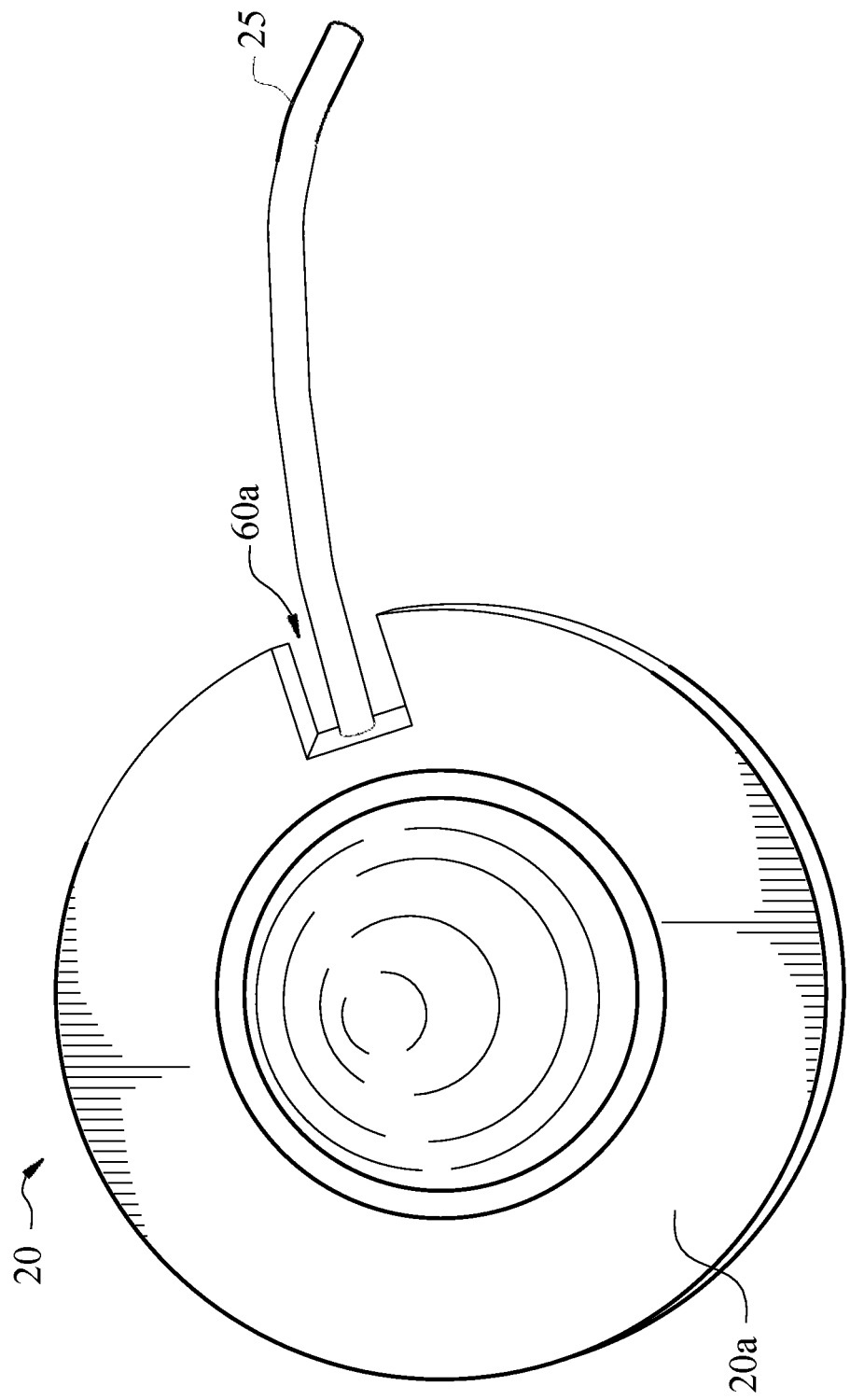
FIG. 2C is a perspective view of the nodule of FIG. 2A in an assembled configuration.

FIGS. 2A-2C depict an example of nodule 20 including top hemisphere 20a separable from bottom hemisphere 20b. Top hemisphere 20a has a thickness that is greater than a thickness of bottom hemisphere 20b, as depicted in the disassembled configuration of nodule 20 shown in FIG. 2A. Each of top hemisphere 20a and bottom hemisphere 20b includes a laterally-disposed notch (first notch 60a and second notch 60b, respectively), within the surface area of the hemisphere. The notches 60a, 60b of each hemisphere are substantially identically shaped and sized, such that in an assembled configuration of nodule 20, the notches 60a, 60b of each hemisphere align to create a singular notch laterally-disposed within a body of nodule 20. The notch is configured to receive pneumatic tube 25 therein (as shown in particular in FIG. 2C), such that pneumatic tube 25 is in fluidic communication with cavity 32 of nodule 20. FIG. 2B in particular depicts channel 62 disposed within the body of bottom hemisphere 20b between notch 60b and cavity 32, such that at least a portion of pneumatic tube 25 is insertable within cavity 32 through the channel, while pneumatic tube 25 is restricted from movement due to the surfaces that define the notch. FIG. 2B also depicts the plurality of granules 34 disposed within cavity 32. When assembled, as shown in FIG. 2C, pressure values within cavity 32 and acting on the plurality of granules 34 can be altered via pneumatic tube 25 that is in fluidic communication with cavity 32. As shown in FIG. 2C, in an embodiment, top hemisphere 20a and bottom hemisphere 20b are secured together, with pneumatic tube 25 secured therein.

Under normal conditions, the plurality of granules 34 flow freely within cavity 32, such that nodule 20 feels soft and pliable. Under vacuum pressure, the plurality of granules 34 jam together and movement is restricted, making nodule 20 stiffer than under normal conditions. Because top hemisphere 20a is thicker than bottom hemisphere 20b, when vacuum pressure is applied to nodule 20, top hemisphere 20a substantially maintains its shape while bottom hemisphere 20b deforms as the plurality of granules 34 are forced toward top hemisphere 20a and away from bottom hemisphere 20b.

Figure 3A:
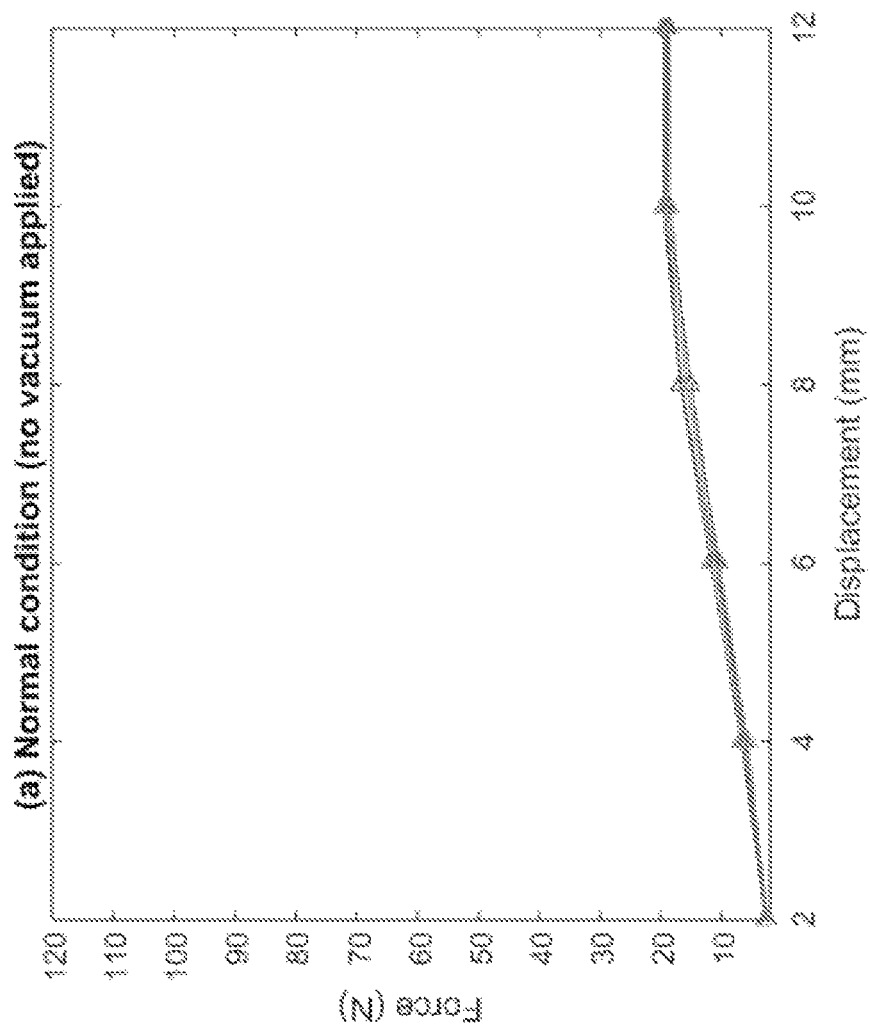
FIG. 3A is a graphical representation of the force-displacement curve of the nodule of FIG. 2A under normal conditions in the absence of a vacuum. The curve shows the reaction force data from 2 mm displacement to 12 mm displacement.
Figure 3B:
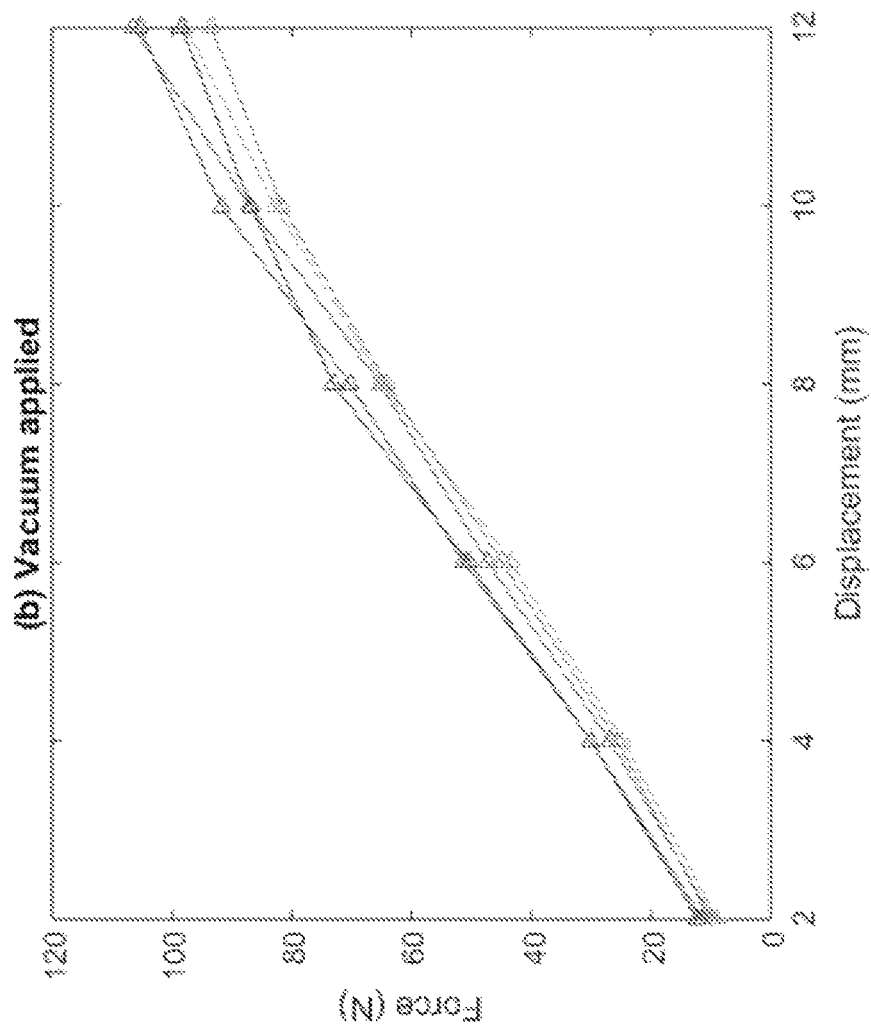
FIG. 3B is a graphical representation of the force-displacement curve of the nodule of FIG. 2A under a vacuum pressure of 4.5 pounds per square inch. The curve shows the reaction force data from 2 mm displacement to 12 mm displacement.

Accordingly, FIGS. 3A-3B are graphical representations of the force-displacement curve of nodule 20 from the examples depicted in FIGS. 2A-2C. A stiffness test was performed on nodule 20 under normal conditions with no vacuum applied (graphically depicted in FIG. 3A), and under vacuum pressure conditions with a pressure of 4.5 pounds per square inch (PSI) applied to cavity 32 to act on the plurality of granules 34 (graphically depicted in FIG. 3B). To test nodule 20, a force gauge was used to exert a force on top hemisphere 20a, with force and displacement values recorded at 2 mm, 4 mm, 6 mm, 8 mm, 10 mm, and 12 mm. The test was repeated five times for each condition (normal and vacuum pressure). As shown in FIGS. 3A-3B, under normal pressure conditions (in the absence of vacuum pressure), very little force is required to displace top hemisphere 20a up to 12 mm, with an upper force value of approximately 20 N required to displace top hemisphere 20a by 12 mm. However, under vacuum pressure conditions, approximately 10 N of force is required to displace top hemisphere 20a by 2 mm, and about 90-100 N of force required to displace top hemisphere 20a by 12 mm.

Figure 4:
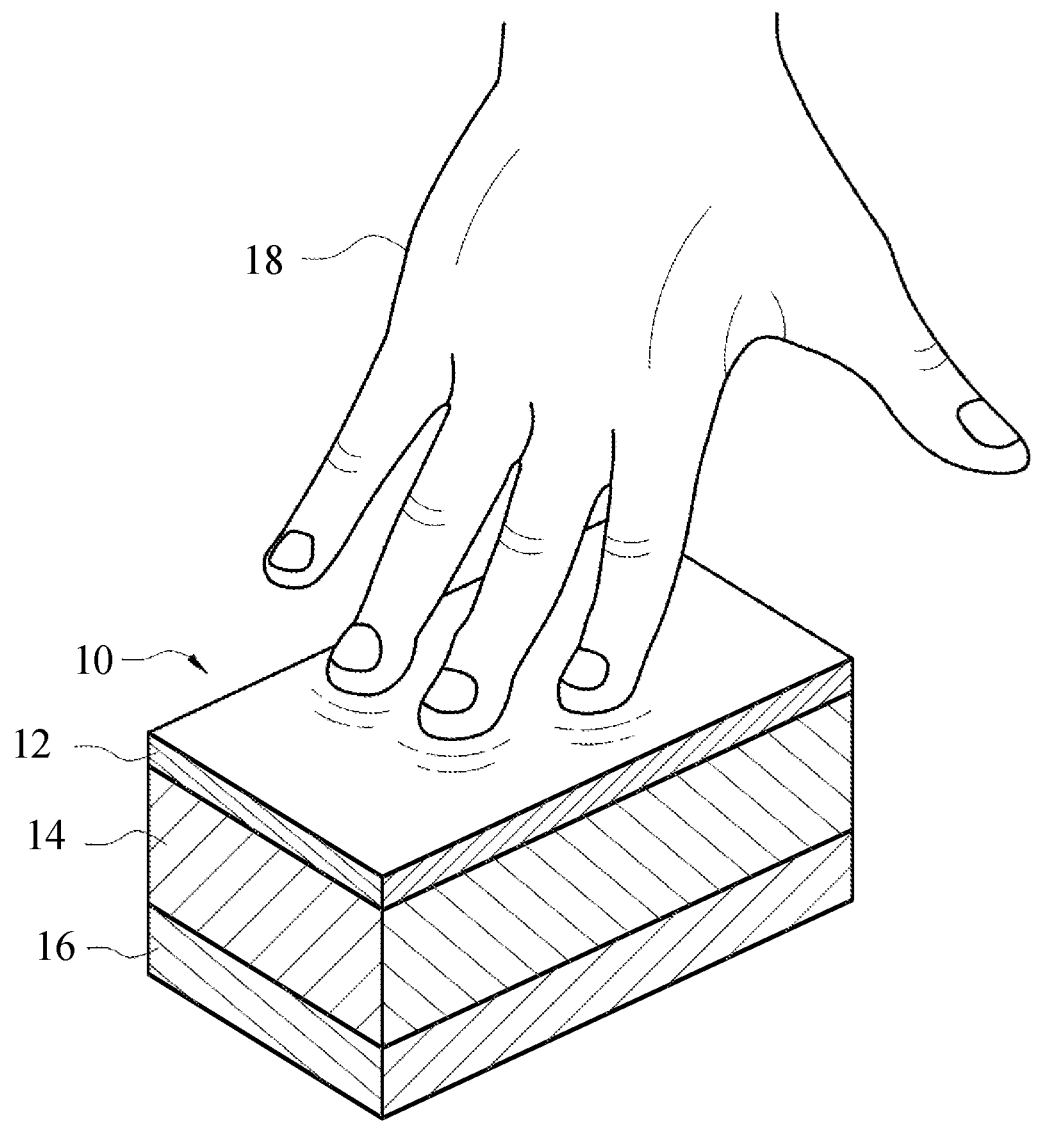
FIG. 4 is a perspective view of a soft tissue phantom apparatus including an embedded tactile display device, in accordance with an embodiment of the present invention.

In an embodiment, nodule 20 is disposed within tactile device 10, which is shown in detail in FIG. 4. Tactile device 10 includes palpation surface 12, phantom layer 14, and control box 16. As will be shown in further figures and described in greater detail below, phantom layer 14 houses nodule 20 that is capable of having varying stiffnesses, such that phantom layer 14 provides different sensations when contacted via palpating surface 12 by a user (represented by hand 18 in FIG. 4). Control box 16 is in mechanical communication with nodule 20 within phantom layer 14 and is utilized to change a stiffness of nodule 20. The components housed within and in communication with tactile device 10 will be described in greater detail below.

Figure 5:
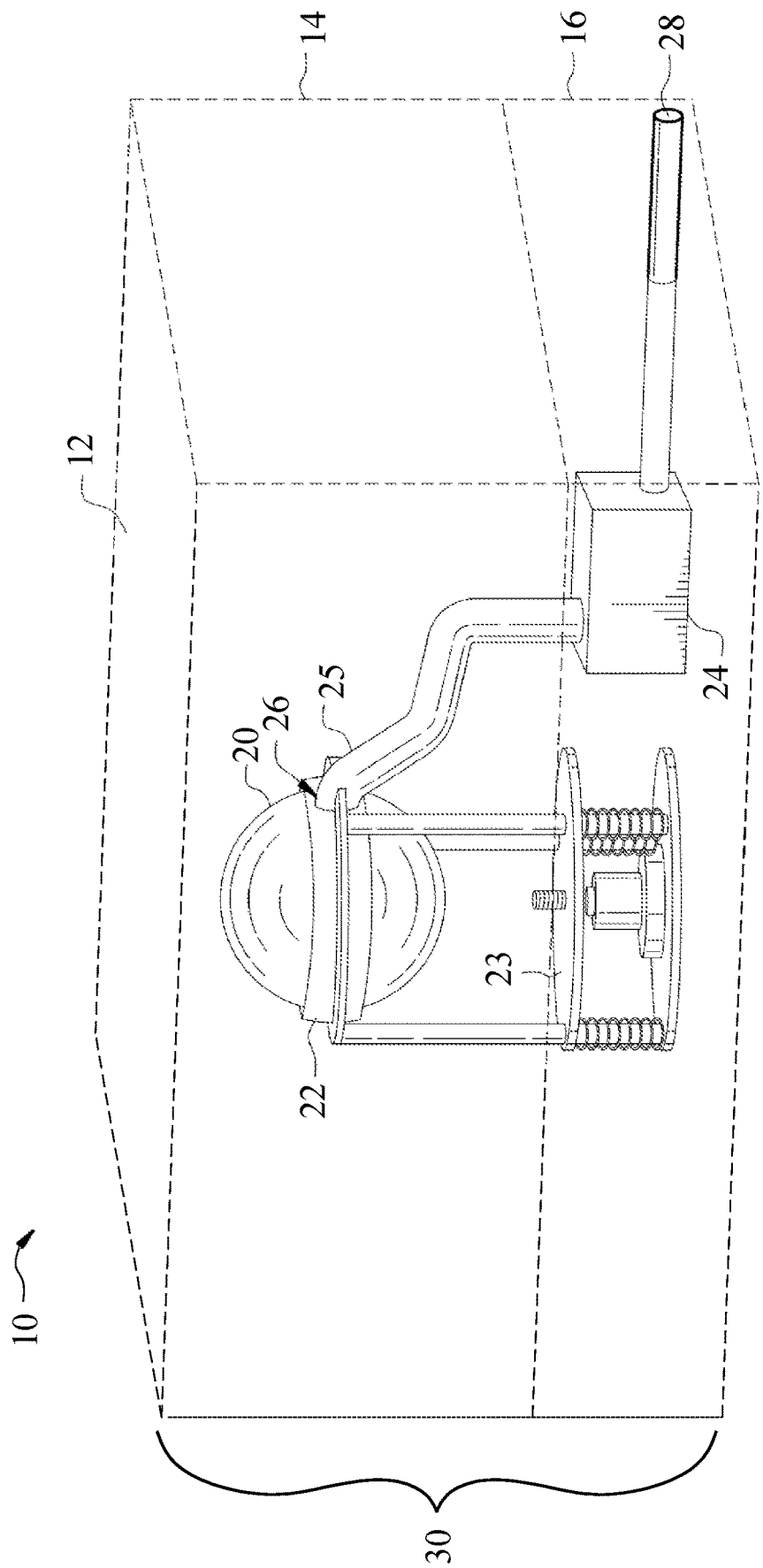
FIG. 5 is a perspective view of a nodule disposed within the soft tissue phantom apparatus of FIG. 4.

As shown in FIG. 5, nodule 20 is disposed within phantom layer 14, which serves as a housing for nodule 20. While FIG. 5 shows one nodule 20 disposed within phantom layer 14, it is contemplated that multiple nodules 20 may be disposed within phantom layer 14, depending on the requirements of the training or telemedicine use of tactile device 10. So that a user can interact with nodule 20 disposed below palpation surface 12 of tactile device, both palpation surface 12 and phantom layer 14 must be compliant, or flexible, such that phantom layer 14 mimics a soft tissue in a human body. Phantom layer 14, together with control box 16, may be referred to as chamber 30, with chamber 30 being a general term to describe the internal components of tactile device 10 disposed below palpation surface 12.

Chamber 30 is designed such that nodule 20 has a variable stiffness, as described in greater detail above, thereby mimicking a region of interest on a patient (either a live patient, in the case of telemedicine, or a virtual patient, in the case of simulation and training). Since nodule 20 has variable stiffness, nodule 20 can be used to mimic different regions of interest within a singular patient, or for different patients, providing a singular, customizable device useful in treating different patients.

To control a position of nodule 20, nodule 20 is disposed proximate to actuator base 23 and is surrounded by support ring 22. Support ring 22 is in mechanical communication with actuator base 23, such that support ring 22 can be translated along a lateral axis of chamber 30 (i.e., in a direction toward palpation surface 12, and in a direction away from palpation surface 12). The translation of support ring 22 may be accomplished by any mechanical means. An example of a translation device shown in FIG. 7 includes a set of springs that can be compressed by a motor in mechanical communication with a lead screw to move actuator base 23 up and down within chamber 30, with the compression of the springs capable of translating support ring 22 (and, thereby, nodule 20) in a direction away from palpation surface 12. Similarly, a decompression of the spring translates support ring 22 and nodule 20 in a direction toward palpation surface 12. The depth of nodule 20 within phantom layer 14 and chamber 30 is an important parameter for palpation, because a user must be able to locate and palpate masses at varying depths within a human patient.

Also disposed within chamber 30, as mentioned above, is control box 16. Control box 16 is in mechanical communication with phantom layer 14, and may be disposed proximate to phantom layer 14, or may be separated from phantom layer 14 by a wall or membrane. In an embodiment, as shown in FIG. 5, control box 16 includes actuator base 23, as well as the associated spring and motor components that function to translate support ring 22 within phantom layer 14. Also disposed within control box 16 is pneumatic control unit 24, which includes an intermediary line leading out of chamber 30 via port 28, and pneumatic tube 25 coupling pneumatic control unit 24 with nodule 20. Port 28 functions as an air inlet and an air outlet to allow air flow into chamber 30 and out of chamber 30, depending on the pressure requirements of nodule 20 at a given time. Pneumatic control unit 24 connects to nodule via pneumatic tube 25 disposed through inlet 26, which provides a port through which air can enter or be removed from a cavity defined by the exterior palpation surfaces of nodule 20.

By utilizing granular jamming, the geometrical properties of nodule 20 (calculated while nodule 20 is not receiving an external force, such as a pushing force from a user) need not change during operation. Instead, nodule 20 can be customized to have different associated stiffnesses by varying the granules within nodule 20, as well as the pressure within nodule 20 as varied by pneumatic control unit 24 via pneumatic tube 25. As such, nodule 20 can be modified without the need to open control box 30 to change a position, shape, or size or nodule 20; instead, the modification is performed via port 28 and inlet 26.

Figure 6:
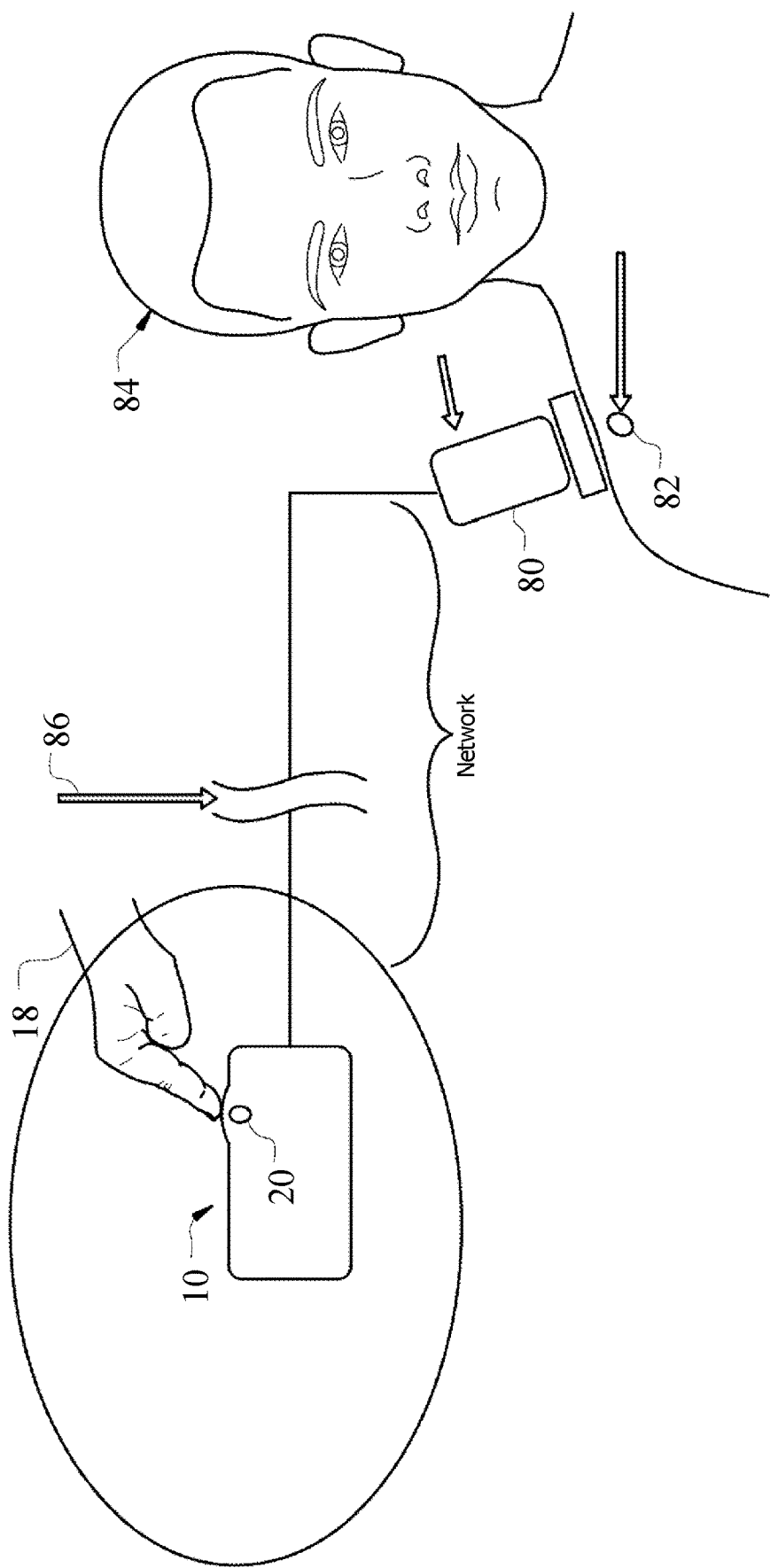
FIG. 6 is a perspective view of a tactile sensor used in a location that is remote from the tactile display device of FIG. 4, with the tactile sensor being in communication with the tactile display device.

FIG. 6 depicts an embodiment of the present invention including sensor 80 that is in wireless communication with tactile display device 10 via network 86, such as by sending a transmission via RF waves from an antenna, the transmission being received by an RF antenna on tactile display device 10. Regardless of the wireless communication protocol, sensor 80 is used in a location remote from nodule 20 to apply a force to a real-life nodule 82 on a real-life patient 84. The force required to palpate real-life nodule 82 on real-life patient 84 is recorded by sensor 80 and transmitted to tactile display device 10 via network 86. The force value received by tactile display device 10 is used to apply a vacuum pressure value to nodule 20 that is selected to match the force required to palpate real-life nodule 82. As such, a physician in a location remote from real-life patient 84 (represented by hand 18 in FIG. 6) can utilize telemedicine by palpating nodule 20 in tactile display device 10 to remotely provide medical advice and diagnostics to real-life patient 84.

Figure 7:
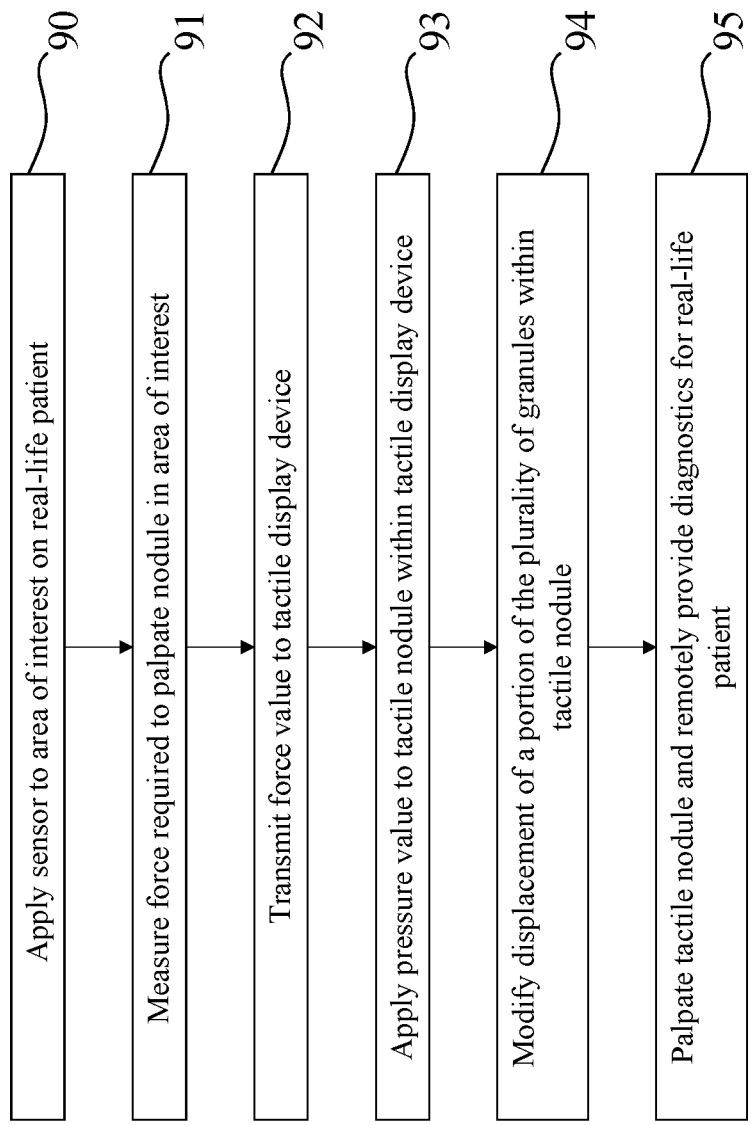
FIG. 7 is a process flow diagram depicting a method of palpating a nodule from a remote location, in accordance with an embodiment of the present invention.

Referring now to FIG. 7, in conjunction with FIGS. 1A-6, an exemplary process-flow diagram is provided, depicting a method of remotely palpating a nodule to provide diagnostics for a real-life nodule on a real-life patient. The steps delineated in the exemplary process-flow diagram of FIG. 7 are merely exemplary of an order of measuring and palpating a nodule from a remote location. The steps may be carried out in another order, with or without additional steps included therein.

As shown in FIG. 7, the method includes step 90, in which a sensor, such as sensor 80, is applied to an area of interest on a real-life patient, the area of interest including a nodule. The sensor measures a force value required to palpate the nodule within the area of interest during step 91. The force value is transmitted to a tactile display device, such as tactile display device 10 described in detail above, during step 92. During step 93, a pressure value is applied to a tactile nodule within the tactile display device, such as tactile nodule 20 within tactile display device 10. The pressure value is selected to mimic the pressure value detected by the sensor and transmitted to the tactile display device. Due to the change in pressure value within the tactile nodule, a portion of the plurality of granules disposed within the tactile nodule are displaced during step 94. Accordingly, during step 95, a physician or care provider can palpate the tactile nodule to indirectly interact with the plurality of granules, such that the physician can remotely palpate the nodule on the real-life patient and provide diagnostics related to the nodule.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

INCORPORATION BY REFERENCE

[1] Paszek, M. J. et al. Tensional homeostasis and the malignant phenotype. Cancer Cell. 2005. Vol. 8(3). 241-54.
[2] Phipps, S. et al. Measurement of tissue mechanical characteristics to distinguish between benign and malignant prostatic disease. Urology. 2005. Vol. 66(2). 447-50.
[3] Williams I I, R. L. et al. The virtual haptic back for palpatory training. 2004.
[4] Jeon, S. et al. Haptic simulation of breast cancer palpation: A case study of haptic augmented reality. IEEE International Symposium on Mixed and Augmented Reality. 2010. 237-38.
[5] Baillie, S. et al. Validation of a bovine rectal palpation simulator for training veterinary students. Stud. Health Technol. Inform. 2005. Vol. 111. 33-36.
[6] Takaiwa, Masahiro and Noritsugu, Toshiro. Development of breast cancer palpation simulator using pneumatic parallel manipulator. SICE Annual Conference 2007. 2007. 823-27.
[7] Gwilliam, J. C. et al. Design and control of an air-jet lump display. 2012 IEEE Haptics Symposium (HAPTICS). 2012. 45-49.

[8] Li, M. et al. A tactile sensing and feedback system for tumor localization. 2016 13th International Conference on Ubiquitous Robots and Ambient Intelligence (URAI). 2016. 259-62.

[9] Li, M. et al. Multi-fingered haptic palpation utilizing granular jamming stiffness feedback actuators. Smart Mater. Struct. 2014. Vol. 23(9). 095007.

[10] Stanley, A. A. et al. Closed-loop shape control of a haptic jamming deformable surface. 2016 IEEE International Conference on Robotics and Automation (ICRA). 2016. 2718-24.

[11] Liu, A. J. et al. Jamming is not just cool any more. Nature. 1998. Vol. 396(6706). 21-22.

[12] Jiang, A. et al. Robotic granular jamming: Does the membrane matter? Soft. Robot. 2014. Vol. 1(3). 192-201.

[13] Cheng, N. G. et al. Design an analysis of a robust, low-cost, highly articulated manipulator enabled by jamming of granular media. 2012 IEEE International Conference on Robotics and Automation. 2012. 4328-33.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

It is also to be understood that the following claims are intended to cover all of the generic and specific features of the invention herein described, and all statements of the scope of the invention that, as a matter of language, might be said to fall therebetween.

What is claimed is:

1. A method of remotely providing a diagnostic to a patient, the method comprising:
    movably affixing at least one sensor to an area of interest on the patient, wherein the at least one sensor is communicatively coupled with a tactile display device, whereby the at least one sensor is configured to measure a value of force applied to at least one real-life nodule within the area of interest of the patient;
    transmitting, into a memory of the tactile display device, the measured force value of the at least one sensor;
    generating, via a processor of the tactile display device, a vacuum pressure value, wherein the vacuum pressure value is configured to mimic the measured force value detected by the at least one sensor;
    palpating, via the processor, a care provider, or both, an exterior palpation surface of the tactile display device based on the vacuum pressure value; and
    automatically transmitting, via the processor, at least one notification indicative of the diagnostic to the patient based on the palpation of the exterior palpation surface of the tactile display device.

2. The method of claim 1, wherein the tactile display device further comprises:
    at least one tactile nodule, wherein the at least one tactile nodule is in mechanical communication with the exterior surface; and
    at least one actuator, wherein the at least one actuator is configured to be in mechanical communication, electrical communication, or both with the at least one tactile nodule, whereby the at least one actuator is disposed beneath the at least one tactile nodule.

3. The method of claim 2, further comprising the step of, translating, via the at least one actuator of the tactile display device, the at least one tactile nodule along a lateral axis of the tactile display device toward and away from the exterior palpation surface of the tactile display device.

4. The method of claim 2, wherein the at least one tactile nodule comprises an interactive side and a base side, and wherein the interactive side extends toward the exterior palpation surface of the tactile display device and the base side extends away from the exterior palpation surface of the tactile display device.

5. The method of claim 4, wherein the interactive side is made from a first material, and wherein the base side is made from a second material.

6. The method of claim 5, wherein the first material has a greater stiffness than a stiffness of the second material.

7. The method of claim 6, further comprising the step of, displacing, via the processor, based on the calculated vacuum pressure value, at least one of a plurality of granules disposed within a cavity of the at least one tactile nodule, wherein the at least one tactile nodule is deformed, whereby at least one portion of the at least one tactile nodule replicates a stiffness of the at least one nodule within the area of interest of the patient.

8. The method of claim 7, wherein the step of displacing at least one of a plurality of granules further comprises the step of, removing, via a pneumatic tube of the tactile display device, an amount of air from the cavity of the at least one tactile nodule based on the calculated vacuum pressure value, wherein the base side experiences a greater deformation than a deformation of the interactive side, whereby at least one of the plurality of granules is disposed substantially within the interactive side of the at least one tactile nodule and is configured to be palpated via the exterior palpation surface of the tactile display device.

9. The method of claim 8, wherein the interactive side maintains an original shape when the amount of air is removed from the cavity.

10. The method of claim 1, wherein the tactile display device is configured to communicate with the at least one sensor via the group consisting of audio broadcasting, television broadcasting, RF waves, radar communication, cellular communication, global position systems (hereinafter "GPS"), Wi-Fi, Bluetooth, and a combination of thereof.

11. The method of claim 1, wherein the at least one sensor is in a location remote from the at least one tactile nodule, the tactile display device, or both.

12. A method of remotely replicating a stiffness of at least one portion of an area of interest of a patient, the method comprising:
    movably affixing at least one sensor to an area of interest on the patient, wherein the at least one sensor is communicatively coupled with a tactile display device, whereby the at least one sensor is configured to measure a value of force applied to the at least one portion of the area of interest of the patient;
    transmitting, into a memory of the tactile display device, the measured force value to a memory of the tactile display device;
    generating, via a processor of the tactile display device, a vacuum pressure value, wherein the vacuum pressure value is configured to mimic the measured force value detected by the at least one sensor; and
    displacing, via the processor, based on the calculated vacuum pressure value, at least one of a plurality of granules disposed within a cavity of at least one tactile nodule, the at least one tactile nodule being in electrical communication with the tactile display device, wherein at least one portion of the at least one tactile nodule is deformed, whereby the at least one portion of the at least one tactile nodule is configured to mimic a stiffness of the at least one portion of the area of interest of the patient.

13. The method of claim 12, wherein the tactile display device comprises an exterior palpation surface in mechanical communication with the at least one tactile nodule, wherein the exterior palpation surface is configured to be interacted with by at least one care provider.

14. The method of claim 13, wherein the at least one tactile nodule comprises an interactive side and a base side, wherein the interactive side is configured to extend toward the exterior palpation surface of the tactile display device.

15. The method of claim 14, wherein the interactive side is made from a first material, and wherein the base side is made from a second material.

16. The method of claim 15, wherein the first material has a greater stiffness than a stiffness of the second material.

17. The method of claim 12, wherein the remote palpation system is configured to communicate with the at least one sensor via the group consisting of audio broadcasting, television broadcasting, RF waves, radar communication, cellular communication, GPS, Wi-Fi, Bluetooth, and a combination of thereof.

18. A remote palpation system comprising:
at least one force sensor;
a tactile display device, wherein the tactile display device comprises at least one tactile nodule;
wherein the tactile display device is configured to receive a measured force value from the at least one force sensor; and
wherein subsequent to receiving the measured force value from the at least one sensor, the at least one tactile nodule of the tactile display device is configured to mimic a stiffness of the real-life nodule on the patient, such that remote diagnostics are performable on the real-life nodule on the patient via the at least one tactile nodule.

19. The remote palpation system of claim 18, wherein the tactile display device further comprises:
a cavity disposed within the at least one tactile nodule, wherein the at least one tactile nodule includes an interactive side opposite a base side, whereby the interactive side and the base side together encase the cavity;
a plurality of granules, wherein the plurality of granules are configured to be disposed within a cavity of the at least one tactile nodule; and
a pneumatic control unit, wherein the pneumatic control unit is configured to input, remove, or both at least one portion of air from the cavity via a pneumatic tube in mechanical communication with the cavity.

20. The remote palpation system of claim 19, wherein the interactive side is made from a first material, and wherein the base side is made from a second material, the first material having a greater stiffness than a stiffness of the second material, wherein, due to a deformation of the at least one tactile nodule resulting from the removal of air from the cavity by the pneumatic control unit, the base side experiences a greater deformation than a deformation of the interactive side, such that the plurality of granules are disposed substantially within the interactive side and are configured to be palpated via the exterior palpation surface.

* * * * *